US 011259864B2

(12) United States Patent
Stamm et al.

(10) Patent No.: US 11,259,864 B2
(45) Date of Patent: Mar. 1, 2022

(54) SURGICAL INSTRUMENT WITH ENHANCED TRIGGER

(71) Applicant: COVIDIEN LP, Mansfield, MA (US)

(72) Inventors: Stephen J. Stamm, Wheat Ridge, CO (US); Subhadeep Saha, Boulder, CO (US); Purvishkumar H. Soni, Longmont, CO (US); Jessica E. C. Olson, Frederick, CO (US); Alyssa M. Sawyer, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 355 days.

(21) Appl. No.: 16/433,473

(22) Filed: Jun. 6, 2019

(65) Prior Publication Data

US 2020/0383720 A1 Dec. 10, 2020

(51) Int. Cl.
| | |
|---|---|
| *A61B 18/12* | (2006.01) |
| *A61B 18/14* | (2006.01) |
| *A61B 18/00* | (2006.01) |
| *A61B 17/34* | (2006.01) |

(52) U.S. Cl.
CPC ...... *A61B 18/1445* (2013.01); *A61B 18/1206* (2013.01); *A61B 17/3421* (2013.01); *A61B 2018/0063* (2013.01); *A61B 2018/00071* (2013.01); *A61B 2018/00589* (2013.01); *A61B 2018/00595* (2013.01); *A61B 2018/126* (2013.01); *A61B 2018/1452* (2013.01)

(58) Field of Classification Search
CPC ........ A61B 17/2909; A61B 2017/2925; A61B 18/1445; A61B 2018/1455
See application file for complete search history.

(56) References Cited

U.S. PATENT DOCUMENTS

| 5,445,638 A | 8/1995 | Rydell et al. |
| 5,458,598 A * | 10/1995 | Feinberg ............ A61B 18/1445 606/205 |
| 5,605,272 A | 2/1997 | Witt et al. |

(Continued)

FOREIGN PATENT DOCUMENTS

| AU | 2004216575 A1 | 4/2005 |
| CA | 2844067 A1 | 9/2014 |

(Continued)

*Primary Examiner* — Daniel W Fowler
(74) *Attorney, Agent, or Firm* — Carter, DeLuca & Farrell LLP

(57) ABSTRACT

An endoscopic bipolar forceps includes a housing having a shaft extending therefrom including an end effector assembly disposed at a distal end thereof having jaw members. A movable handle is pivotable relative to the housing from an initial position wherein the jaw members are spaced relative to one another to a compressed position wherein the jaw members are closed about tissue. A trigger assembly is pivotably coupled to the movable handle and includes a trigger operably coupled to a knife assembly having a knife, a knife drive bar and a cam pin. The trigger includes an elongated slot defined therein configured to house the cam pin for translation therein. Upon actuation of the movable handle, the trigger moves in unison with the movable handle to the compressed position and the cam pin rides within the elongated slot maintaining consistent angle between the movable handle and the trigger during movement thereof.

11 Claims, 2 Drawing Sheets

(56) References Cited

U.S. PATENT DOCUMENTS

| | | | |
|---|---|---|---|
| 5,817,093 A * | 10/1998 | Williamson, IV | A61B 17/07207 606/50 |
| 5,891,142 A | 4/1999 | Eggers et al. | |
| 5,919,206 A | 7/1999 | Gengler et al. | |
| 5,935,126 A | 8/1999 | Riza | |
| 6,033,399 A | 3/2000 | Gines | |
| 6,077,287 A | 6/2000 | Taylor et al. | |
| 6,129,740 A | 10/2000 | Michelson | |
| 6,187,003 B1 | 2/2001 | Buysse et al. | |
| 6,322,579 B1 | 11/2001 | Muller | |
| 6,334,860 B1 | 1/2002 | Dorn | |
| 6,443,968 B1 | 9/2002 | Holthaus et al. | |
| 6,506,208 B2 | 1/2003 | Hunt et al. | |
| 6,706,056 B2 | 3/2004 | Bacher | |
| 6,770,072 B1 | 8/2004 | Truckai et al. | |
| 6,790,217 B2 | 9/2004 | Schulze et al. | |
| 6,887,240 B1 | 5/2005 | Lands et al. | |
| 7,052,496 B2 | 5/2006 | Yamauchi | |
| 7,090,673 B2 | 8/2006 | Dycus et al. | |
| 7,137,980 B2 | 11/2006 | Buysse et al. | |
| 7,147,638 B2 | 12/2006 | Chapman et al. | |
| 7,150,097 B2 | 12/2006 | Sremcich et al. | |
| 7,384,420 B2 | 6/2008 | Dycus et al. | |
| 7,441,685 B1 | 10/2008 | Boudreaux | |
| 7,494,501 B2 | 2/2009 | Ahlberg et al. | |
| 7,549,988 B2 | 6/2009 | Eberi et al. | |
| 7,559,940 B2 | 7/2009 | McGuire et al. | |
| 7,753,909 B2 | 7/2010 | Chapman et al. | |
| 7,758,608 B2 | 7/2010 | DiCesare et al. | |
| 7,766,910 B2 | 8/2010 | Hixson et al. | |
| 7,877,853 B2 | 2/2011 | Unger et al. | |
| 7,922,953 B2 | 4/2011 | Guerra | |
| 8,241,320 B2 | 8/2012 | Lyons et al. | |
| 8,252,021 B2 | 8/2012 | Boulnois et al. | |
| 8,256,080 B2 | 9/2012 | Cunningham et al. | |
| 8,266,783 B2 | 9/2012 | Brandt et al. | |
| 8,388,646 B2 | 3/2013 | Chojin | |
| 8,394,094 B2 | 3/2013 | Edwards et al. | |
| 8,409,244 B2 | 4/2013 | Hinman et al. | |
| 8,545,534 B2 | 10/2013 | Ahlberg et al. | |
| 8,551,090 B2 | 10/2013 | Sutter et al. | |
| 8,647,341 B2 | 2/2014 | Dycus et al. | |
| 8,728,118 B2 | 5/2014 | Hinman et al. | |
| 8,740,933 B2 | 6/2014 | Anderson | |
| 8,789,741 B2 | 7/2014 | Baxter, III et al. | |
| 8,814,856 B2 | 8/2014 | Elmouelhi et al. | |
| 8,828,023 B2 | 9/2014 | Neff et al. | |
| 8,858,553 B2 | 10/2014 | Chojin | |
| 9,408,660 B2 | 8/2016 | Strobl | |
| 9,918,780 B2 | 3/2018 | Allen, IV et al. | |
| 2004/0087943 A1 * | 5/2004 | Dycus | A61B 17/2909 606/51 |
| 2005/0090837 A1 | 4/2005 | Sixto et al. | |
| 2010/0063525 A1 | 3/2010 | Beaupre et al. | |
| 2011/0071522 A1 * | 3/2011 | Dumbauld | A61B 18/1445 606/45 |
| 2011/0270251 A1 | 11/2011 | Horner et al. | |
| 2012/0116416 A1 | 5/2012 | Neff | |
| 2013/0053831 A1 * | 2/2013 | Johnson | A61B 17/2909 606/1 |
| 2014/0025073 A1 | 1/2014 | Twomey et al. | |

FOREIGN PATENT DOCUMENTS

| | | |
|---|---|---|
| EP | 2319447 A1 | 5/2011 |
| WO | 2016025132 A1 | 2/2016 |

* cited by examiner

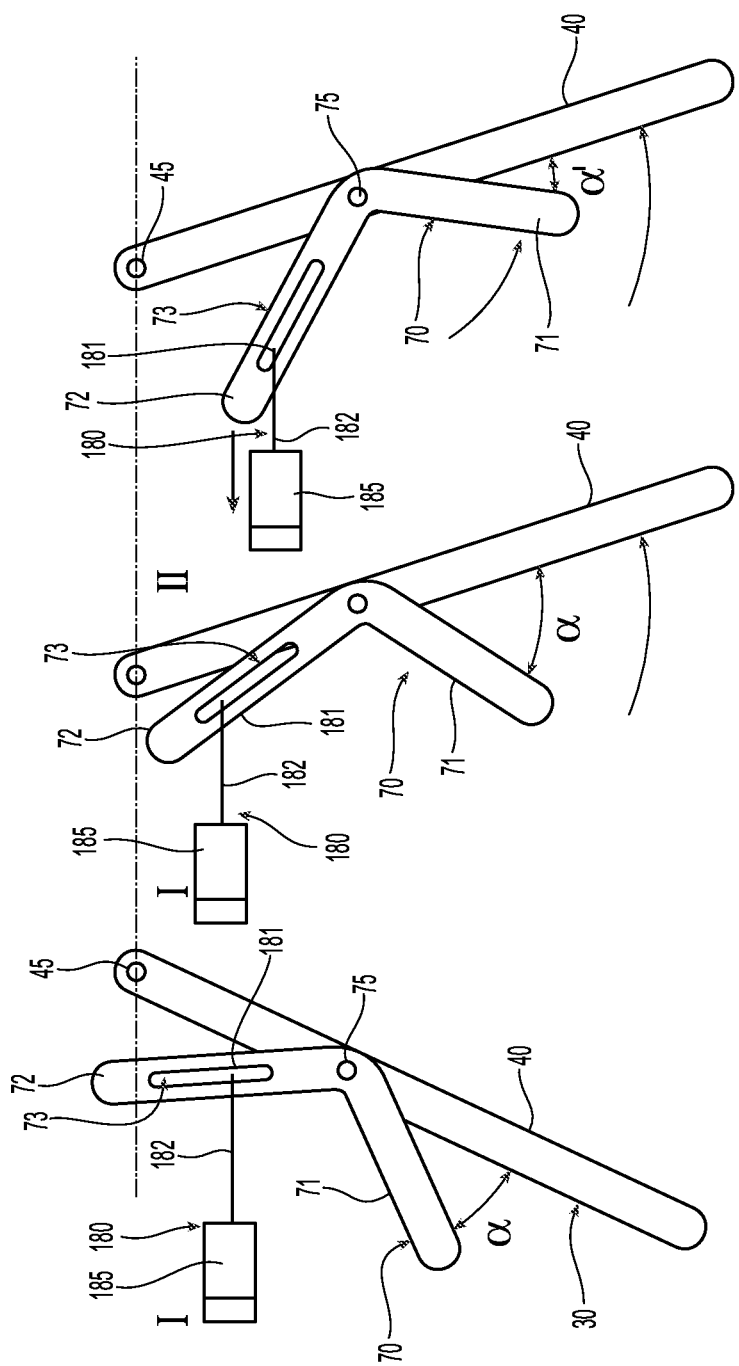

SURGICAL INSTRUMENT WITH ENHANCED TRIGGER

BACKGROUND

Technical Field

The present disclosure relates to endoscopic surgical instruments and, more particularly, to endoscopic surgical instruments for treating and cutting tissue.

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic forceps are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

Typically, endoscopic forceps include a trigger that is operably associated with the instrument housing that may be selectively actuated to cut tissue either prior to or after tissue treatment. Various trigger assemblies and configurations have been developed that facilitate actuation of a cutting mechanism to cut tissue disposed between jaw members of an end effector assembly or to advance a cutting mechanism or electrode relative to a distal end of the forceps. By and large, these trigger assemblies include a pivot or pivot assembly that is based within the housing to enable the trigger to pivot relative thereto. In addition, the trigger is typically independently moveable relative to the housing.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A endoscopic bipolar forceps provided in accordance with aspects of the present disclosure includes a housing having a shaft extending therefrom having an end effector assembly disposed at a distal end thereof including first and second jaw members. A movable handle is selectively pivotable relative to the housing from an initial position wherein the first and second jaw members are disposed in spaced relation relative to one another to a compressed position wherein the first and second jaw members are closed about tissue. A trigger assembly is pivotably coupled to the movable handle and includes a trigger operably coupled to a knife assembly including a knife, a knife drive bar and a cam pin. The trigger includes an elongated slot defined therein configured to house the cam pin for translation therein.

Upon actuation of the movable handle relative to the housing, the trigger moves in unison with the movable handle to the compressed position and the cam pin rides within the elongated slot maintaining an angle alpha ($\alpha$) between the movable handle and the trigger during movement thereof.

In aspects according to the present disclosure, the trigger is poised for actuation relative to the movable handle when the movable handle is disposed in the compressed position. In other aspects according to the present disclosure, actuation of the trigger relative to the movable handle forces the cam pin distally within the elongated slot which, in turn, forces the knife drive bar to actuate the knife.

In aspects according to the present disclosure, the angle alpha ($\alpha$) between the movable handle and the trigger is maintained within the range of about 0 degrees to about 40 degrees during actuation of the movable handle.

In other aspects according to the present disclosure, the end effector assembly includes a knife channel defined therein for translating the knife therethrough, the cam pin configured to bottom out within the elongated slot prior to the knife contacting a distal-most edge of the knife channel.

In yet other aspects according to the present disclosure, a switch is operably associated with the housing and in electromechanical cooperation with a source of electrosurgical energy, the switch allowing a user to selectively supply electrosurgical energy to the jaw members to effect a tissue seal.

In still other aspects according to the present disclosure, a rotating assembly is included and is configured to allow selective rotation of the end effector assembly.

A trigger assembly for an endoscopic bipolar forceps is also provided in accordance with aspects of the present disclosure includes a trigger pivotably coupled to a movable handle of the endoscopic bipolar forceps. The trigger is operably coupled to a knife assembly having a knife, a knife drive bar and a cam pin. The trigger includes an elongated slot defined therein configured to house the cam pin for translation therein. Upon actuation of the movable handle relative to a housing of the endoscopic bipolar forceps, the trigger moves in unison with the movable handle as the movable handle moves to a compressed position relative to the housing while the cam pin rides within the elongated slot maintaining an angle alpha ($\alpha$) between the movable handle and the trigger during movement thereof.

In aspects according to the present disclosure, the trigger is poised for actuation relative to the movable handle when the movable handle is disposed in the compressed position. In other aspects according to the present disclosure, actuation of the trigger relative to the movable handle forces the cam pin distally within the elongated slot which, in turn, forces the knife drive bar to actuate the knife.

In yet other aspects according to the present disclosure, the angle alpha ($\alpha$) between the movable handle and the trigger is maintained within the range of about 0 degrees to about 40 degrees during actuation of the movable handle.

BRIEF DESCRIPTION OF THE DRAWINGS

Various embodiments of the subject instrument are described herein with reference to the drawings wherein:

FIG. 2A is a schematic illustration of a movable handle and a trigger assembly of the surgical instrument of FIG. 1 wherein the movable handle is disposed in an initial, spaced apart position relative to the housing and the trigger is unactuated and disposed at an angle alpha ($\alpha$) relative to the movable handle;

FIG. 2B is a schematic illustration of the movable handle and the trigger assembly of the surgical instrument of FIG. 1 wherein the movable handle is disposed in a compressed position relative to the housing and the trigger is unactuated and disposed at the same angle alpha ($\alpha$) relative to the movable handle; and FIG. 2C is a schematic illustration of the movable handle and the trigger assembly of the surgical instrument of FIG. 1 wherein the movable handle is disposed in the compressed position relative to the housing and the trigger is actuated and disposed at an angle alpha ($\alpha'$) relative to the movable handle

DETAILED DESCRIPTION

Figure 1:
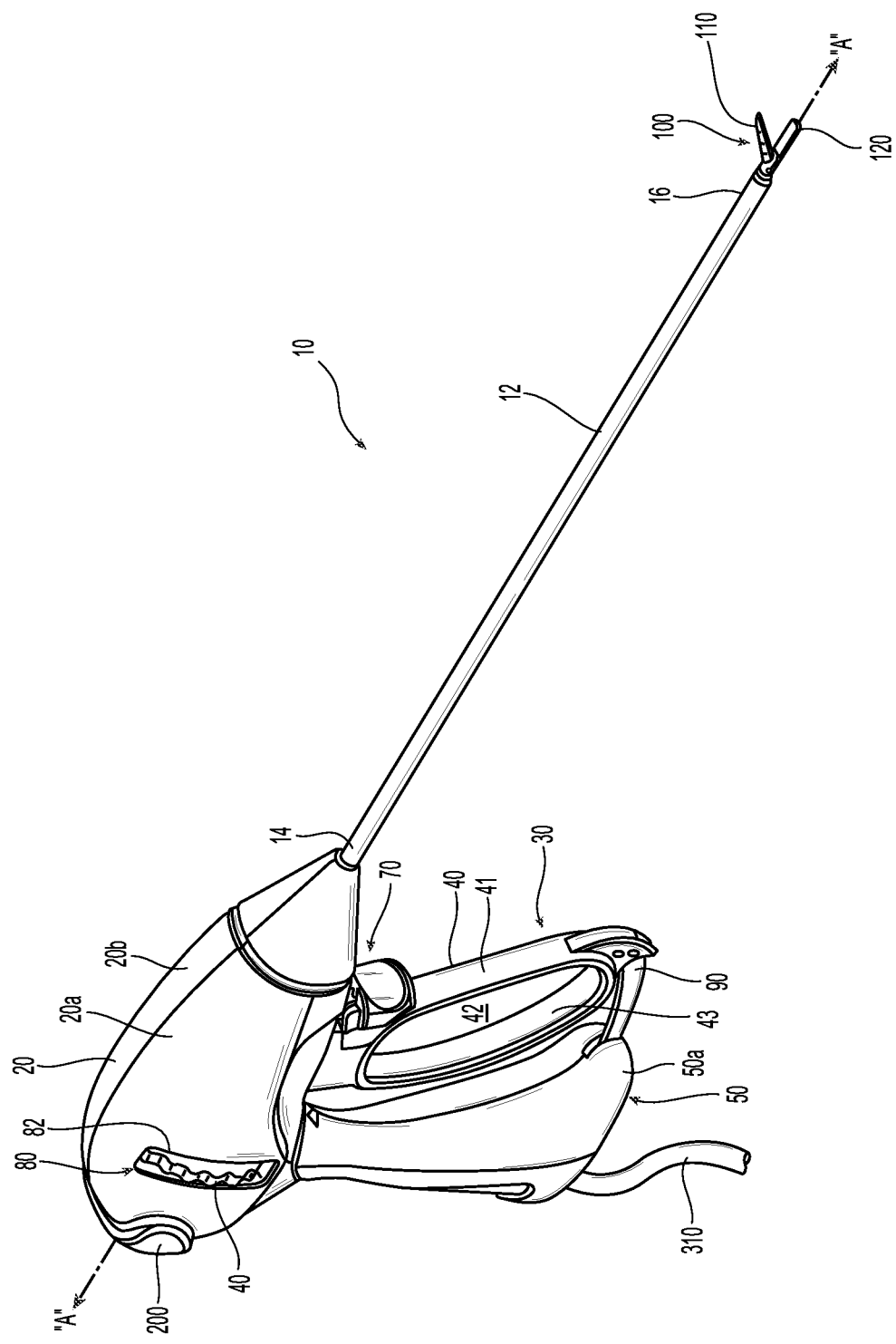
FIG. 1 is a right, perspective view of an endoscopic bipolar forceps showing a housing, a shaft and an end effector assembly according to the present disclosure.

Turning now to FIG. 1, one embodiment of an endoscopic bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide tubular vessels and vascular tissue. Forceps 10 includes a shaft 12 which has a distal end 16 dimensioned to mechanically engage the end effector assembly 100 and a proximal end 14 which mechanically engages the housing 20. Details of how the shaft 12 connects to the end effector are not described in detail but may be found in U.S. Pat. No. 8,647,341 the entire contents of which is incorporated by reference herein.

The proximal end 14 of shaft 12 is received within the housing 20 and the connections relating thereto are described in detail with respect to the above-identified U.S. Pat. No. 8,647,341. Forceps 10 also includes an electrosurgical cable 310 which connects the forceps 10 to a source of electrosurgical energy, e.g., a generator (not shown). Generators such as those sold by Covidien—a division of Medtronic, may be used as a source of electrosurgical energy, e.g., FX8 Energy Platform, FT10 Energy Platform, ForceTriad™ Energy Platform, LS10 Generator, FORCE EZ™ Electrosurgical Generator, FORCE FX™ Electrosurgical Generator, FORCE 1C™, FORCE 2™ Generator, SurgiStat™ Low Energy Electrosurgical Generator. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS" the entire contents of which is also incorporated by reference herein.

Handle assembly 30 includes a fixed handle 50 and a movable handle 40. Fixed handle 50 is integrally associated with housing 20 and handle 40 is movable relative to fixed handle 50. Rotating assembly 80 is integrally associated with the housing 20 and is rotatable approximately 180 degrees in either direction about a longitudinal axis defined through shaft 12.

Housing 20 is formed from two (2) housing halves 20a and 20b which each include a plurality of interfaces dimensioned to mechanically align and engage one another to form housing 20 and enclose the internal working components of forceps 10. As can be appreciated, fixed handle 50 which, as mentioned above, is integrally associated with housing 20, takes shape upon the assembly of the housing halves 20a and 20b. Movable handle 40 and trigger assembly 70 are typically made of unitary construction and are operatively connected to the housing 20 and the fixed handle 50 during the assembly process.

End effector assembly 100 is attached at the distal end 16 of shaft 12 and includes a pair of opposing jaw members 110 and 120. Movable handle 40 of handle assembly 30 is ultimately connected to a drive assembly (not shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. Rotating assembly 80 allows selective rotation of the end effector assembly 100.

Turning now to the more detailed features of the present disclosure as described with respect to FIG. 1, movable handle 40 includes a finger loop 41 which has an aperture 42 defined therethrough which enables a user to grasp and move the handle 40 relative to the fixed handle 50. Handle 40 also includes an ergonomically-enhanced gripping element 43 disposed along the inner peripheral edge of aperture 42 which is designed to facilitate gripping of the movable handle 40 during activation. Gripping element 43 may include one or more protuberances, scallops and/or ribs to enhance gripping. Movable handle 40 is selectively moveable about one or more pivots (not shown) from a first position relative to fixed handle 50 to a second position in closer proximity to the fixed handle 50 which, as explained below, imparts movement of the jaw members 110 and 120 relative to one another.

As explained in more detail with respect to the above-identified U.S. Pat. No. 8,647,341, the movable handle 40 includes a clevis (not shown) that moves about a pivot 45 (FIGS. 2A-2C) and cooperates with the drive assembly (not shown) to impart movement of the jaw members 110, 120 relative to one another. The lower end of the movable handle 40 includes a flange 90 having a distal end (not shown) that rides within a predefined channel (not shown) disposed within fixed handle 50 to lock the movable handle 40 relative to the fixed handle 50.

End effector assembly 100 includes opposing jaw members 110, 120 which cooperate to effectively grasp tissue for sealing purposes. Actuation of the drive assembly causes jaw member 110 to move unilaterally relative to jaw member 120 to close jaw member 110 about tissue. Jaw members 110, 120 may also be designed as a bilateral jaw assembly wherein both jaw members 110, 120 move relative to one another upon actuation of the drive assembly.

Jaw members 110, 120 may be opened, closed and rotated to manipulate tissue until sealing is desired. This enables the user to position and re-position the forceps 10 prior to activation and sealing. The end effector assembly 100 is rotatable about longitudinal axis A-A defined through the forceps. Trigger assembly 70 includes an L-shaped trigger 71 that mounts to movable handle 40 about a pivot 75 and cooperates with a knife assembly 180 to selectively translate a knife 185 through a formed tissue seal (FIGS. 2A-2C). Knife assembly 180 includes a knife drive rod 182 that connects to the knife 185 at a distal end thereof and a cam pin 181 at a proximal end thereof. L-shaped trigger includes an elongated slot 73 defined therein that is configured to receive cam pin 181 of the knife assembly. As explained in further detail below, actuation of the trigger 71 relative to the movable handle 40 actuates the knife 185 through tissue.

Turing now FIGS. 2A-2C, the relative movement of the movable handle 40 and the trigger assembly 70 is schematically illustrated. Movable handle 40 is selectively movable about pivot 45 between a first position wherein the movable handle 40 is disposed in spaced relation relative to handle 50 (FIG. 2A) to a compressed position closer to handle 50 (FIG. 2B). In the first position, the jaw members 110, 120 are disposed in a corresponding spaced apart orientation relative to one another and the knife 185 is disposed proximal to the jaw members 110, 120. Cam pin 181 is disposed in an at rest position towards the lower portion of the elongated slot 73.

Initial actuation of the movable handle 40 towards the handle 50 about pivot pin 45, forces drive assembly (not shown) to translate a corresponding drive rod (not shown) to move the jaw members 110, 120 to close about tissue disposed therebetween. Details relating to the drive assembly are explained with respect to the above-referenced, commonly-owned U.S. Pat. No. 8,647,341 the entire contents of which is incorporated by reference herein.

Once the desired position for the sealing site is determined and the jaw members 110, 120 are properly positioned, movable handle 40 is compressed to close the jaw members 110, 120 about tissue and apply the necessary closure pressure to tissue within a range of about 3 kg/cm$^2$ to about 15 kg/cm$^2$. Flange 90 may be configured to lock movable handle 40 relative to handle 50 as explained in detail with respect to the above-referenced, commonly-owned U.S. Pat. No. 8,647,341 the entire contents of which is incorporated by reference herein. Once locked (or fully compressed and held), jaw members 110, 120 are fully compressed about the tissue and forceps 10 is now ready for selective application of electrosurgical energy via a switch 200 and subsequent separation of the tissue via advancement of the knife 185.

As movable handle 40 is actuated from the initial position (FIG. 2A) and moved towards handle 50, cam pin 181 rides distally along elongated slot 73 of trigger 71. During movement thereof, the knife 185 remains at bay in the proximal position relative to the jaw members 110, 120. As the movable handle 40 moves, the angle alpha ($\alpha$) relative to trigger 71 remains the same until the movable handle 40 is fully compressed and the jaw members 110, 120 close and compress the tissue (FIG. 2B).

Switch 200, disposed atop housing 20, is configured to permit the user to selectively activate the forceps 10 when the jaw members 110, 120 are closed about the tissue. When switch 200 is depressed, electrosurgical energy is transferred to jaw members 110, 120, respectively and through tissue to form a tissue seal.

Once sealed, the knife 185 is selectively deployed to cut the tissue along the tissue seal. More particularly, when the movable handle 40 is disposed in a fully actuated position (FIG. 2B), the trigger 71 is poised for selective actuation relative to movable handle 40. Actuation of the trigger 71 relative to movable handle 40 about pivot 75, forces the cam pin 181 distally which, in turn, forces the knife drive rod 182 and knife 185 distally to cut tissue disposed between the jaw members 110, 120. Cam pin 181 may be dimensioned to bottom out within elongated slot 73 which may act as a knife stop and prevent the knife 185 from contacting a distal-most edge of the knife channel (not shown) disposed between jaw members 110, 120. As a result, the knife edge is protected from unnecessary wear and tear. Details relating to a similar knife assembly and a knife channel disposed between the jaw members 110, 120 are explained with respect to the above-referenced, commonly-owned U.S. Pat. No. 8,647, 341 the entire contents of which is incorporated by reference herein.

The angle alpha ($\alpha$) relative to movable handle 40 and the resulting angle alpha prime ($\alpha'$) relative to movable handle 40 when trigger 71 is fully actuated (See FIG. 2C) may be dimensioned to correspond to a 1:1 ratio of the distance the cam pin 181 travels along elongated slot 73 relative to the distance that the trigger 71 moves along an arc segment. Other ratios are envisioned depending upon a particular purpose. A spring or other biasing member (not shown) may be operably associated with the trigger 71 to return the trigger 71 to an unactuated position (FIG. 2B) upon release of the trigger 71. In embodiments, the angle alpha ($\alpha$) between the movable handle 40 and the trigger 71 is in the range of about 0 degrees to about 40 degrees.

A safety switch or circuit (not shown) may be employed such that the switch 200 cannot fire unless the jaw members 110 and 120 are closed and/or unless the jaw members 110, 120 have tissue held therebetween. Various safety mechanisms and feedback systems are described in commonly-owned U.S. Pat. No. 7,137,980 entitled "METHOD AND SYSTEM FOR CONTROLLING OUTPUT OF RF MEDICAL GENERATOR" the entire contents of which are hereby incorporated by reference herein.

Once the desired position for the sealing site is determined and the jaw members 110, 120 are properly positioned, movable handle 40 may be compressed to close the jaw members 110, 120 about tissue and apply the necessary closure pressure to tissue within a range of about 3 kg/cm$^2$ to about 15 kg/cm$^2$. Flange 90 may be configured to lock movable handle 40 relative to handle 50 as explained in detail with respect to the above-referenced, commonly-owned U.S. Pat. No. 8,647,341 the entire contents of which is incorporated by reference herein. Once locked (or fully compressed and held), jaw members 110, 120 are fully compressed about the tissue and forceps 10 is now ready for selective application of electrosurgical energy via switch 200 and subsequent separation of the tissue via advancement of the knife 185 via trigger 71.

One or both jaw members, e.g., jaw member 120, may include a stop member (not shown) which limits the movement of the two opposing jaw members 110, 120 relative to one another. The stop member extends from one or both sealing surfaces of the jaw members 110, 120 a predetermined distance according to the specific material properties (e.g., compressive strength, thermal expansion, etc.) to yield a consistent and accurate gap distance "G" during sealing. The gap distance between opposing sealing surfaces during sealing ranges from about 0.001 inches to about 0.006 inches and, preferably, between about 0.002 and about 0.003 inches. As energy is being selectively transferred to the end effector assembly 100, across the jaw members 110, 120 and through the tissue, a tissue seal forms. Once formed, the knife 185 may be advanced via trigger 71 to divide the tissue along the tissue seal. Details relating to the stop member(s)

are described in the above commonly-owned U.S. Pat. No. 8,647,341 the entire contents of which is incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic bipolar forceps, comprising:
   a housing;
   a shaft extending from the housing having an end effector assembly disposed at a distal end thereof including first and second jaw members;
   a movable handle selectively pivotable relative to the housing from an initial position wherein the first and second jaw members are disposed in spaced relation relative to one another to a compressed position wherein the first and second jaw members are closed about tissue; and
   a trigger assembly pivotably coupled to the movable handle, the trigger assembly including a trigger defining a first member and a second member extending at an angle with respect to the first member, the trigger operably coupled to a knife assembly including a knife, a knife drive bar and a cam pin, the trigger including an elongated slot defined therein configured to house the cam pin for translation therein,
   wherein, upon actuation of the movable handle relative to the housing, the trigger moves in unison with the movable handle to the compressed position and the cam pin rides within the elongated slot maintaining an angle alpha ($\alpha$) between the movable handle and the trigger during movement thereof.

2. The endoscopic bipolar forceps according to claim 1, wherein the trigger is poised for actuation relative to the movable handle when the movable handle is disposed in the compressed position.

3. The endoscopic bipolar forceps according to claim 1, wherein actuation of the trigger relative to the movable handle forces the cam pin distally within the elongated slot which, in turn, forces the knife drive bar to actuate the knife.

4. The endoscopic bipolar forceps according to claim 1, wherein the angle alpha ($\alpha$) between the movable handle and the trigger is maintained within the range of about 0 degrees to about 40 degrees during actuation of the movable handle.

5. The endoscopic bipolar forceps according to claim 1, wherein the end effector assembly includes a knife channel defined therein for translating the knife therethrough, the cam pin configured to bottom out within the elongated slot prior to the knife contacting a distal-most edge of the knife channel.

6. The endoscopic bipolar forceps according to claim 1, further comprising a switch operably associated with the housing and in electromechanical cooperation with a source of electrosurgical energy, the switch allowing a user to selectively supply electrosurgical energy to the jaw members to effect a tissue seal.

7. The endoscopic bipolar forceps according to claim 1, further comprising a rotating assembly configured to allow selective rotation of the end effector assembly.

8. A trigger assembly for an endoscopic bipolar forceps, comprising:
   a trigger defining a first member and a second member extending at an angle with respect to the first member, the trigger pivotably coupled to a movable handle of the endoscopic bipolar forceps, the trigger operably coupled to a knife assembly including a knife, a knife drive bar and a cam pin, the trigger including an elongated slot defined therein configured to house the cam pin for translation therein,
   wherein, upon actuation of the movable handle relative to a housing of the endoscopic bipolar forceps, the trigger moves in unison with the movable handle as the movable handle moves to a compressed position relative to the housing while the cam pin rides within the elongated slot maintaining an angle alpha (α) between the movable handle and the trigger during movement thereof.

9. The trigger assembly for an endoscopic bipolar forceps claim 8, wherein the trigger is poised for actuation relative to the movable handle when the movable handle is disposed in the compressed position.

10. The trigger assembly for an endoscopic bipolar forceps claim 8, wherein actuation of the trigger relative to the movable handle forces the cam pin distally within the elongated slot which, in turn, forces the knife drive bar to actuate the knife.

11. The trigger assembly for an endoscopic bipolar forceps claim 8, wherein the angle alpha (α) between the movable handle and the trigger is maintained within the range of about 0 degrees to about 40 degrees during actuation of the movable handle.

\* \* \* \* \*